United States Patent [19]

Wagatsuma et al.

[11] Patent Number: 5,976,810
[45] Date of Patent: Nov. 2, 1999

[54] METHOD OF DETECTING AUTOANTIBODY PRESENT IN THE SERUM OF RHEUMATIC

[75] Inventors: Masako Wagatsuma; Michio Kimrua; Hiroshi Watanabe, all of Saitama; Fujio Takeuchi, Shizuoka, all of Japan

[73] Assignee: Hoechst Pharmaceuticals & Chemicals K.K., Tokyo, Japan

[21] Appl. No.: 08/793,937

[22] PCT Filed: Sep. 7, 1995

[86] PCT No.: PCT/JP95/01776

§ 371 Date: May 8, 1997

§ 102(e) Date: May 8, 1997

[87] PCT Pub. No.: WO96/07914

PCT Pub. Date: Mar. 14, 1996

[30] Foreign Application Priority Data

Sep. 8, 1994 [JP] Japan .................................. 6-239640

[51] Int. Cl.$^6$ ..................... G01N 33/53; G01N 33/564
[52] U.S. Cl. ..................... 435/7.1; 436/506; 436/509; 530/389.1; 530/350
[58] Field of Search ............... 435/7.1; 436/506, 436/509; 530/389.1, 350

[56] References Cited

FOREIGN PATENT DOCUMENTS 1131462 5/1989 Japan .

OTHER PUBLICATIONS

Anthony Bretscher, "Purification of an 80,000–dalton PRotein That is a Component of the Isolated Microvillus Cytoskeleton, and Its Localization in Nonmuscle Cells," *J. Cell Biol.*, vol. 97, pp. 425–432 (1983).

Kathleen L. Gould et al., "cDNA Cloning and Sequencing of the Protein–Tyrosine Kinase Substrate, Ezrin, Reveals Homology to Band 4.1" *The EMBO Journal*, vol. 8, No. 13, pp. 4133–4142 (1989).

Sachiko Tsukita et al., "A New 82–kD Barbed End–capping Protein (Radixin) Localized in the Cell–to–Cell Adherens Junction: Purification and Characterization," *J. Cell Biol.*, vol. 108, pp. 2369–2382 (19890.

Noriko Funayama et al., "Radixin Is a Novel Member of the Band 4.1 Family," *J. Cell Biol.*, vol. 115, No. 4, pp. 1039–1048 (1991).

Wolfgang Lankes et al., "A Heparin–Binding Protein Involved in Inhibition of Smooth–Muscle Cell Proliferation," *Biochem. J.*, 251:831–842 (1988).

Wolfgang Lankes et al., "Moesin: A Member of the Protein 4.1–Talin–Ezrin Family of Proteins," *Proc. Natl. Acad. Sci. USA*, vol. 88, pp. 8297–8301 (1991).

Naruki Sato et al., "A Gene Family Consisting of Ezrin, Radixin and Moesin—Its Specific Localization at Actin Filament/plasma Membrane Association Sites," *J. Cell Sci.*, vol. 103, pp. 131–143 (1992).

Mark Egerton et al., "Identification of Ezrin as an 81–kDa Tyrosine–Phosphorylated Protein in T Cells," *J. Immunol.*, vol. 149, pp. 1847–1852 (1992).

Ossi Turunen et al., "Cytovillin, a Microvillar Mr 75,000 Protein," *J. Biological Chemistry*, vol. 264, No. 28, pp. 16727–16732 (1989).

*Primary Examiner*—Frank C. Eisenschenk
*Assistant Examiner*—Evelyn Rabin
*Attorney, Agent, or Firm*—Finnegan, Henderson, Farabow, Garrett & Dunner, L.L.P.

[57] ABSTRACT

A reagent for immunologically detecting rheumatism containing as an antigen at least one mammalian protein selected from among ezrin, radixin and moesin and/or a peptide composed of at least nine consecutive amino acid residues found in the amino acid sequences of ezrin, radixin and moesin; and a method of detecting autoantibodies present in the serum of a rheumatic. An immunological reaction using this reagent enables precritical or early diagnosis of rheumatism. An immunological detection using the above autoantigenic proteins is convenient and reliable as an early serodiagnostic method based on rheumatism-specific antigens.

4 Claims, 5 Drawing Sheets

———— 100 μm

———— 100 μm

METHOD OF DETECTING AUTOANTIBODY PRESENT IN THE SERUM OF RHEUMATIC

This application is a national stage application of PCT JP95/01776 filed Sep. 7, 1995.

BACKGROUND OF THE INVENTION

1. Field of the Invention

This invention relates to a method of immunologically-detecting rheumatism and a reagent of immunologically detecting therefor. In more detail, it relates to a method of immunologically detecting antibodies which react with autoantigenic proteins present in the serum of a rheumatic patient and a reagent therefor.

2. Description of the Prior Art

Rheumatism is a chronic systemic inflammatory autoimmune disease that causes swelling and pain in the multi-joints and malaise, infirmity, weight loss, febricula and anorexia in other body organs. Criteria for the classification of rheumatoid established by American Rheumatoid Association have been currently used in clinical diagnoses (Arnet, F. C. et al. Arthritis Rheum. vol. 305, Abstract 45, 1987); (1) morning stiffness, (2) arthritis of 3 or more joint areas, (3) arthritis of hand joints, (4) symmetric arthritis, (5) radiographic changes, (6) serum rheumatoid factor, (7) rheumatoid nodules. For the classification purposes, a patient shall be diagnosed to have rheumatism if he/she has satisfied at lease 4 of these 7 criteria. Moreover, by examining blood, there are chronic inflammatory symptoms such as acceleration of erythrocyte sedimentation rate and increase of C-reative protein reaction in the sera. There are also special symptoms such as anemia, increase of white blood cells, increase of thrombocytes, increase of γ-globulin in sera. However, all the diagnosis are applied to patients after the occurrence of some symptoms. Therefore, it has long been desired that a new method should be established enabling to diagnose patients before the occurrence of the clinical symptoms or with early staged symptoms. The present invention attempts to find an early diagnosis of rheumatism before the obvious occurrence of the symptoms. This invention relates to a method of detecting a serum based on rheumatic specific antigens at the early stage and it is considered highly useful for its convenience and reliability.

DETAILED DESCRIPTION OF THE INVENTION

From the point of view that rheumatism is an autoimmune disease and that focusing at autoantibodies present in the serum of a rheumatic patient, the present invention attempts to detect autoantibodies which reacts with specific autoantigens. The inventors of the present invention found that ezrin, radixin and moesin were antigen substances which reacted with the autoantibodies present in the serum of a rheumatic patient, which led to the completion of the invention.

Therefore, the present invention provides for a method of detecting autoantibodies present in the serum of a rheumatic patient by reacting one or more proteins selected from the group consisting of ezrin, radixin and moesin of mammalian origin and/or one or more peptides comprising at least 9 or more consecutive amino acid residues in an amino acid sequence derived from ezrin, radixin and moesin with human sera. Although ezrin, radixin, moesin which are derived from mammalian origin are applicable, those derived from human are specially more preferable.

Autoantigen substances containing one or more than two various kinds can be used for the detection.

The present invention provides for a method of detecting autoantibodies present in the serum of a rheumatic patient by reacting radixin with human sera, a method of detecting autoantibodies present in the serum of a rheumatic patient by reacting radixin and moesin with human sera, and a method of detecting autoantibodies present in the serum of a rheumatic patient by reacting ezrin, radixin and moesin with human sera.

Further, the present invention relates to a reagent for immunologically detecting rheumatism containing as an antigen at least one mammalian protein selected from the group of ezrin, radixin and moesin and/or a peptide composed of at least nine consecutive amino acid residues Further, the present invention provides for a reagent for immunologically detecting rheumatism containing radixin as an antigen, a reagent for immunologically detecting rheumatism containing radixin and moesin as an antigen, and a reagent for immunologically detecting rheumatism containing ezrin, radixin and moesin as an antigen.

Further, the present invention provides for a reagent for immunologically detecting rheumatism containing a peptide composed of at least nine consecutive amino acid residues found in the amino acid sequences of radixin as an antigen, a reagent for immunologically detecting rheumatism containing a peptide composed of at least nine consecutive amino acid residues found in the amino acid sequences of moesin as an antigen, and a reagent for immunologically detecting rheumatism containing a peptide composed of at least nine consecutive amino acid residues found in the amino acid sequences of ezrin as an antigen.

The present invention has a great advantage in that it enables to detect rheumatism by a convenient method of isolating the serum and measuring the amount of antibodies. On the other hand, the conventional diagnosis of rheumatism mainly depends on the occurrence of the clinical symptoms.

The autoantibodies against varioius nuclear antigens are detected in the sera of patients with autoimmune diseases, and they are known to be closely related to the clinical symptoms. Recently, it has been disclosed that corresponding antigens (autoantigens) against many autoantibodies are giant molecules in the cells and that they are proteins which are conserved beyond species. The present invention at first attempted to detect tissues which reacted with the serum of a rheumatic patient by using a frozen mouse whole body section for the purpose of isolating and identifying unknown autoantigens which reacted with autoantibodies in the serum of a rheumatic patient. As a result, there found an reactive portion in cytoplasm in hypertrophic chondrocytes of mouse cartilage. Then, in order to identify the reactive portion in a molecular level, a method of isolating proteins were established. By applying the method, it was found that not only mouse cartilage but also mouse brain, mouse spleen and mouse liver had a relevant protein. Moreover, it became clear that the cell lines such as MG63 cell which was derived from human osteosarcoma, HepG2 cell which was derived from human liver cancer or 3T6 cell which was derived from mouse embryo had a relevant protein. It was demonstrated that these proteins were conserved beyond the species. It was demonstrated that these proteins were moleculs with 80 kD and 77 kD by Coomassie brilliant blue staining. By Western blot analysis with the serum of a rheumatic patient, a band with 80 kD reacted with the serum of a rheumatic patient by about 33% out of the total sera of rheumatic patients. It was found that a band with 77 kD reacted with the serum of a rheumatic patient by 30% out of those sera which reacted with 80 kD. It was further found that the band with 80 kD was separated into two bands with 81 kD and 80 kD when the concentration of the gel of the band was reduced to 7%. It was further identified that by analysing amino acid sequences of the proteins, the 81 kD protein was radixin which was derived from a mammalian protein, the 80 kD protein was ezrin and the 77 kD protein was moesin. These proteins belong to a same protein family (Ezrin Radixin Moesin: ERM family) with linking to cytoskeleton.

Ezrin is a protein which was identified in an intestinal brush border microvilli by Bretsher et al in 1983 (J. Cell Biol., vol. 97, p.425–432, 1983), and its full nucleotide sequences were determined by the cloning of the cDNA in 1989 (Gould, K. L. et al., EMBO J., vol., p.4133–4142, 1989; Turunen, O. et al., J. Biol. Chem., vol. 264, p.16727–16732, 1989).

Radixin is a protein which adheres to a barbed end of an actin and localized in the undercoat of a cell-cell adhesions junction or in a border in the period of cytokinesis, but its function remains unknown (Tsukita, S. et al., J. Cell Biol, vol. 108, p.2369–2382, 1989). It was demonstrated by the cloning of the cDNA that it consisted of 4,241 basic pairs in mouse coding for 583 amino acids (Funayama, N. et al., J. Cell Biol., vol. 115, p. 1039–1048, 1991).

Moesin was isolated in a bovine uterus as a membrane-organizing extension spike protein and it was suggested a receptor protein of heparin sulfate (Lankes, W. T. et al., Biochem. J., vol. 251, p.831–842, 1988). It is reported that it consists of 577 amino acids in human by cloning the cDNA (Lankes, W. T. et al., Proc. Natl. Acad. Sci., vol., p.8297–8301, 1991). Recently it has been reported that moesin exists with an actin in an end of villi of an endothelial cell or some epithelial cell but its function remains unknown.

Compared the amino acid sequences of radixin and moesin in mouse with those of ezrin, the homology of the sequences of amino acids 20–280 of the N-terminus was extremely high by 84% and 83%, respectively, and the homology of the sequences of amino acids 280 and more of C-terminus was relatively high by 67% and 62%, respectively, which considered that they belong to the ERM family. Moreover, compared Band 4.1 protein of a red blood cell with ezrin, the homology of the sequences of amino acids 20–280 of the N-terminus was 31%, which leads the ERM family belong to Band 4.1 superfamily (Sato, N., et al., J. Cell Sci., vol. 103, p.131–143, 1992). Since Band 4.1 protein is known to have a function of acting on an actin network by way of spectrin, radixin and moesin are expected to act as a key protein in binding a cell membrane protein with an actin filament. However, it has never been reported that these proteins exist as autoantigens in the serum of a rheumatic patient.

The present invention is applied to the fact that ezrin, radixin and moesin may be possible autoantigens of rheumatism and they react with autoantibodies in the serum of a rheumatic patient. Namely, it provides for a method of detecting autoantibodies in the serum of a rheumatic patient by using ezrin, radixin and moesin as antigens. It enables to measure with ease autoantibodies in the serum of a rheumatic patient by an antigen-antibody reaction as antigens comprising one or more proteins selected from the group consisting of ezrin, radixin and moesin.

Ezrin, radixin and moesin can be produced by isolating from a natural organs such as spleen, uterus and kidney. These proteins can also be produced by a genetic engineering technology by using the cDNA encoding the proteins.

Ezrin, radixin and moesin can be used to detect autoantibodies of rheumatism alone or more than two simultaneously.

Whole molecules of ezrin, radixin and moesin can be used to detect autoantibodies of rheumatism. Alternatively, a fragment of the molecules can be used for the detection of the antibodies. Namely, autoantibodies of rheumatism can be detected by using a peptide comprising at least 9 or more consecutive amino acid residues in the amino acid sequences derived from the proteins as an antigen. For details, a peptide which shows a high antigen-antibody reactivity by ELISA is applied for the detection. The preferable residues of the amino acid sequences as for radixin are shown in SEQ ID NO:1 of the sequence listing and those as for moesin are shown in SEQ ID NO:2 and SEQ ID NO:3 of the sequence listing.

For detection of autoantibodies in the serum of a rheumatic patient by an antigen-antibody reaction, various conventional immunologically methods can be used such as a method of directly measuring a reaction in a liquid phase and a solid phase and a method of measuring an inhibitory reaction immunologically by adding an inhibiting substance. The following are the examples of the above-mentioned detecting methods, (1) aggregation reaction; antigens are spread on the surface of blood cells or gelatin powders, by adding a serum sample, an antigen-antibody reaction occurs and it allows to make an aggregation clot, (2) DID: double immune diffusion method (Octarony method); an extract solution containing antigens and a sample are diffused in a gelatin gel and allows a precipitation reaction, (3) purified antigens are absorbed onto the solid phase, add a serum sample and allow to react, i) ELISA: enzyme linked immunoabsorbent assay; second antibodies bound with an enzyme further allow to react and the amount of colored substance is measured by using a detector, ii) FIA: fluorescent immunosorbent assay; second antibodies bound with a fluorescent dye further allow to react and the amount of fluorescence is measured by using a detector, or iii) CLIA: chemical linked immunosorbent assay; second antibodies bound with a chemiuminescenscent substance further allow to react and the amount of chemiuminescence is measured by using a detector, (4) Nephlometry method: a surface of a latex particle or a glass ball is covered by an antigen, a light is focused at the aggregation reaction solution when encountering said particle and the antibody, and the amount of the transparent light or the scattering light is measured, in addition, the aggregation reaction is similarly measured when encountering solutionized antigens with an antibody without a solid carrier, (5) RIA: radioimmuno assay; second antibodies labeled with a radioisotope further allow to react and the antigen-antibody reaction is detected, (6) immunofluorescent method; a frozen thin slice of tissues containing antigens or cells are fixed on a slide-glass, a serum sample is dropped on the slice and allows to react and further allows to react with second antibodies bound with fluorescent dye and the amount of fluorescence is detected by a microscope.

The inventors of the present invention used the full sequences or partial sequences of the proteins which were produced by a genetic engineering technology as an antigen by way of anti-ezrin antibodies, anti-radixin antibodies and anti-moesin antibodies, and detected autoantibodies in the serum of a rheumatic patient at the early stage, which led to the completion of the invention.

BRIEF DESCRIPTION OF THE DRAWINGS

FIG. 1(1) is a microgram of a sample that a mouse whole body section was reacted with the serum of a healthy subject and then stained and FIG. 1(2) is a microgram of a sample that a mouse whole body section was reacted with the serum of a rheumatic patient and then stained.

FIG. 2(1) is a photo of the electrophoresis pattern which was stained with Coomassie brilliant blue and FIG. 2(2) is a photo of the Western blot analysis with the serum of a rheumatic patient.

BEST MODE FOR ENABLEMENT OF THE INVENTION

This invention shall be more illustratively explained by way of the following Examples. However, this invention shall not be limited by the Examples.

EXAMPLE 1

Immunohistochemical Staining of Mouse Frozen Tissue Sections

Figure 1:
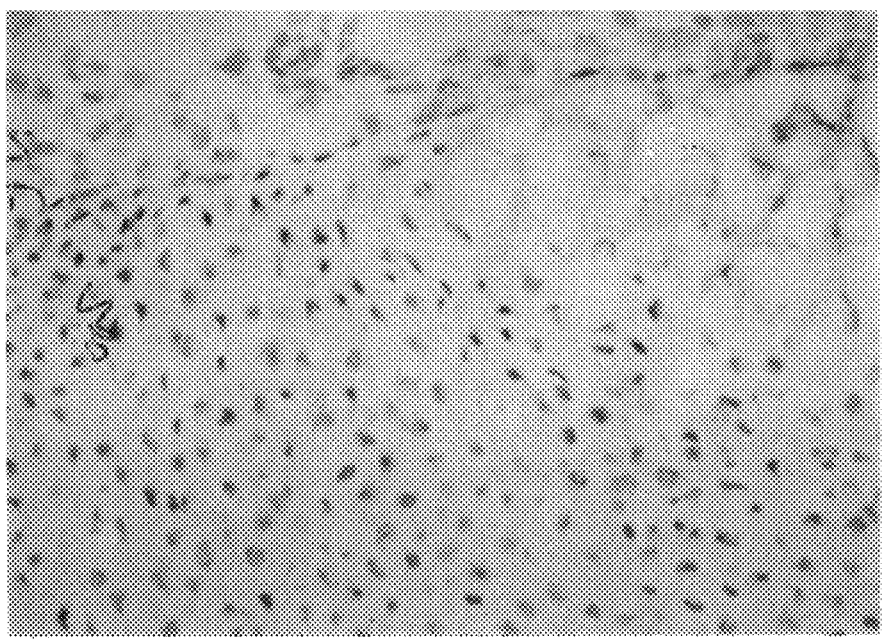
FIGS. 1(1) and 1(2) are micrograms of a preparation that a mouse whole body section was reacted with the serum of a rheumatic patient or a healthy subject and then stained immunohistochemically.
Figure 1:
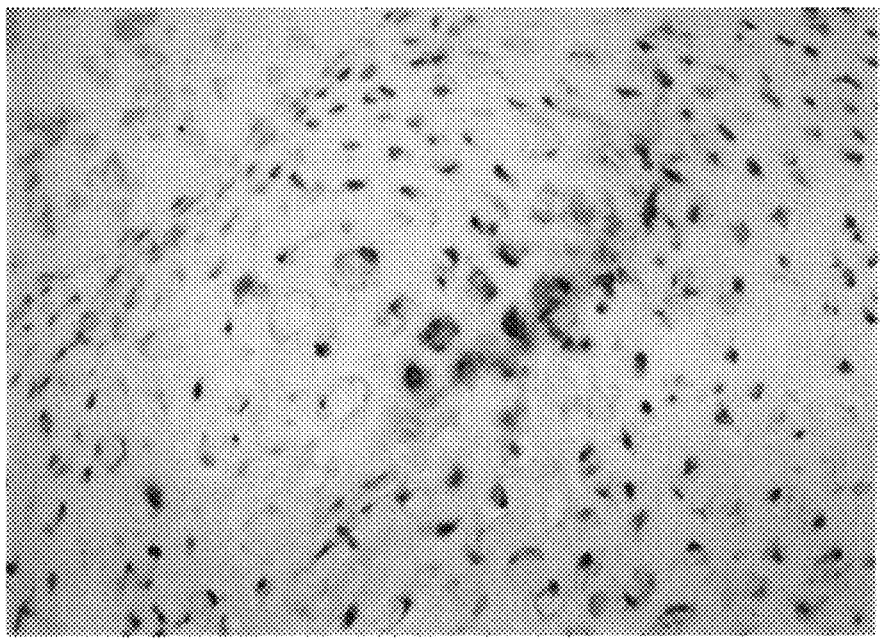

Neonatal ICR mice at the age of 2 days were frozen without fixing, followed by the preparation of frozen tissue sections of 5 μm in thickness by cutting along with a cryostat. The sections were affixed to a slide glass and dried. They were fixed by treating with cold acetone for 5 minutes, the slide glass was soaked in methanol solution containing 0.5% $H_2O_2$ for 30 minutes. Then the slide glass was soaked with water and PBS washing solution (50 mM $Na_2PO_3$, pH 7.4, 0.3M NaCl, 0.1% Tween 20) once, respectively, and then blocked with 300 μl of a blocking buffer (PBS washing solution containing 2% rabbit normal serum) for 15 minutes. Then the slides were reacted with the diluted serum of a patient with rheumatoid arthritis or the serum of a healthy subject, reacted for 30 minutes with 300 μl of the solution which is diluted from 100 times to 1600 times with the blocking buffer (primary antibody), and washed out with the PBS buffer three times for 5 minutes and reacted with 300 μl of biotin-labeled anti-human IgG (rabbit); DAKO A/S which was diluted 200 times with the same solution (secondary antibody) at room temperature for 30 minutes. Next, it was reacted for 30 minutes with 300 μl of streptoavidin-peroxidase-labeled buffer (DAKO A/S) which was diluted 400 time. Then, as described, it was washed out with the PBS buffer three times for 5 minutes and washed with water and put in a DAB reaction solution (50 mM Tris-HCl pH 7.6, 0.01% 3,3'-diaminobenzidine tetrahydrochloride, 0.016% $H_2O_2$) to develop color. Then, it was washed out with water two times, put in a Meyer-hematoxylin solution for 10 seconds, rinsed off with water, put in 0.01% $Na_2CO_3$ solution for 20 seconds and rinsed off with water. After it was stained, the resulting solution was dehydrated with ethanol, ethanol/xylene mixed solution, and xylene, dried in the air, sealed with HSR sealing buffer (Green Gross Co., Ltd.), and then detected by a microscope. As a result, there was an reactive region found in cytoplasm of hypertrophic chondrocytes in mouse cartilage with the patient serum. The result is shown in FIG. 1. FIG. 1 is a microgram of the preparation that a mouse whole body section was reacted with the serum of a patient with rheumatoid arthritis or a healthy subject and then stained immunohistochemically. FIG. 1(1) is a microgram of a sample that a mouse whole body section was reacted with the serum of a healthy subject and then stained and FIG. 1(2) is a microgram of the preparation that a mouse whole body section was reacted with the serum of a patient with rheumatoid arthritis and then stained.

EXAMPLE 2

Partial Purification of Antigen Protein

Using rib cartilage, brain, liver and spleen of the neonatal ICR mice at the age of 2 days, 3T6 cells derived from mouse embryo, HepG2 cells derived from human hepatoma and MG63 cells from human osteosarcoma as starting materials, the following experiments were performed.

One hundred mg of the starting materials was homogenized in 1400 μl of the isotonic buffer (150 mM NaCl, 50 mM sodium phosphate pH 7.4, 10 mM N-ethylmaleimide, 100 mM ε-amino n-caproic acid, 10 mM benzamidine hydrochloride, 5 mM phenylmethylsulfonyl fluoride). The tissues were ground in a mortar and the cells were homogenized in an Eppendorf tube. Then, the nuclei and matrix proteins were removed by centrifugation at 15,000 rpm for 15 minutes and the lysate was subjected to ethanol-precipitation; it was added a half volume of ethanol, stood in dry ice cold-ethanol (–80° C.) for 5 minutes. Then the resulting was unfrozen and centrifuged at 15,000 rpm for 15 minutes. After centrifugation the precipitate was dissolved in 1400 μl of 600 mM sodium acetate (pH 7.0) and precipitated again with a half volume of ethanol. After removal of the precipitate, another half volume of ethanol was added to the lysate and the final precipitate was used as a partially purified fraction for analysis.

EXAMPLE 3

Antigen-Antibody Reaction by Western Blot Analysis

The partially purified fraction obtained as described was dissolved in a sample application buffer (62.5 mM Tris-HCl pH 6.8, 10% glycerol, 5% β-mercaptoethanol, 0.001% bromophenol blue and 2% SDS). Ten μl of the sample per well was loaded on 10% polyacrylamide gel and was electrophoresed in a buffer (25 mM Tris-HCl, 192 mM glycin pH 8.4) containing 0.1% SDS. One portion of the gel was stained with Coomassie brilliant blue (CBB) (Quick CBB: Wako Pure Chemical Inc.) and detected the molecular size of the band. The other was transferred onto a nitrocellulose filter (S&S, BA85) in the electrophoresis buffer containing 20% methanol, at 60 V for 2.5 hours.

The nitrocellulose filter was soaked in a casein A buffer (0.5% casein, 10 mM Tris-HCl pH 7.5, 154 mM NaCl) and stood overnight at 4° C. to be blocked. Next, the resulting filter was reacted with the serum of the patient or a healthy subject which was diluted (1:100) with the casein A buffer at room temperature for 1 or 2 hours. Then, the resulting filter was washed out with Dulbecco's PBS (137 mN NaCl, 1.4 mM potassium phosphate, 4.3 mM sodium phosphate, 2.7 mM KCl) four times and then reacted with biotin-labeled sheep anti-human IgG (TAGO Co. Ltd.) which was diluted 5,000 times with a casein B buffer (0.5% casein, 10 mM Tris-HC, 154 mM NaCl pH 7.4, 0.2% phenol, 0.0008% phenol red) at room temperature for one hour.

Figure 2:
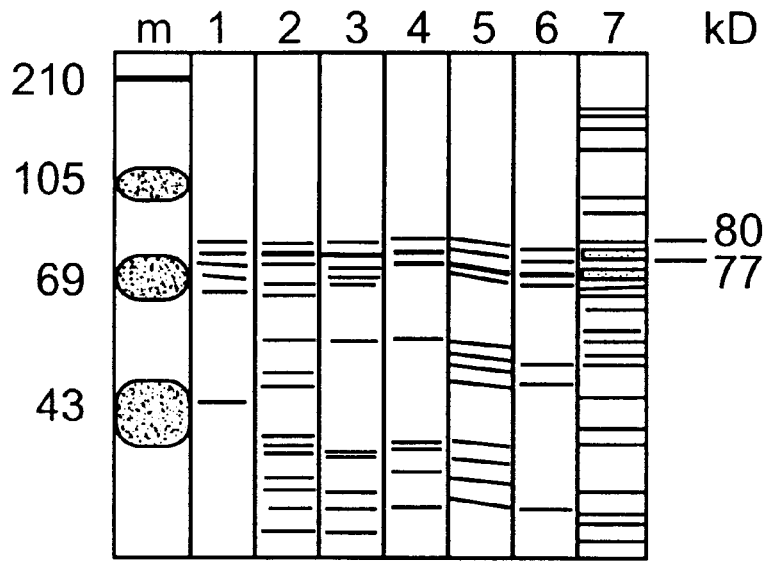
FIGS. 2(1) and 1(2) are photos of the electrophoresis pattern of a partially purified antigen fraction from various animal tissues and cells.
Figure 2:
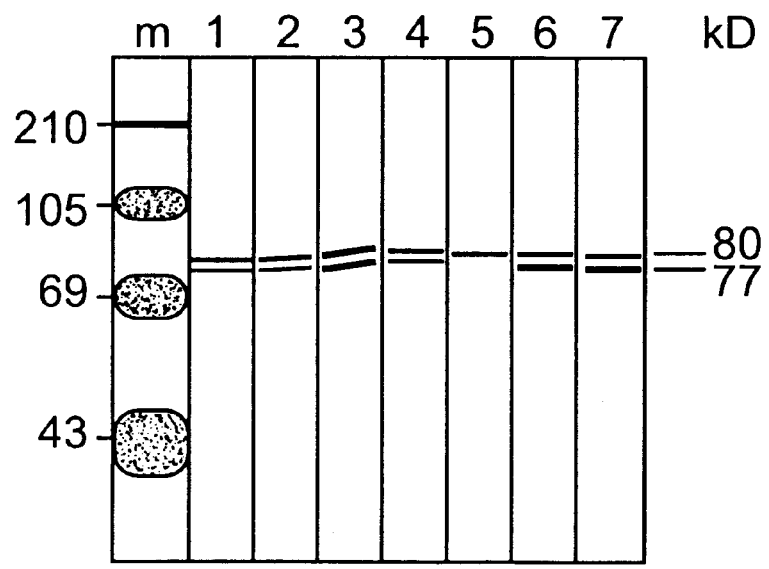

Further, the resulting filter was washed with Dulbecco's PBS four times and reacted with streptoavidin-peroxidase labeled buffer (Cosmobio Co.) which was diluted 500 times with the casein B buffer for one hour and then washed again as described. Next, it was carried out to develop color with 0.03% 4-chloronaphthol staining buffer (20 mM Tris-HCl pH 7.6, 500 mM NaCl). Then it was demonstrated that the sizes of the bands which were reacted with the serum of the patient with rheumatoid arthritis (No. 20) were 80 kD and 77 kD. The result is shown in FIG. 2. In FIG. 2, lane m is a molecular-size marker, lane 1 is mouse brain, lane 2 is mouse liver, lane 3 is mouse spleen, lane 4 is mouse rib cartilage, lane 5 is HepG2 cells derived from human hepatoma, lane 6 is MG63 cells derived from human osteosarcoma, and lane 7 is 3T6 cells derived from mouse embryo.

Figure 3:
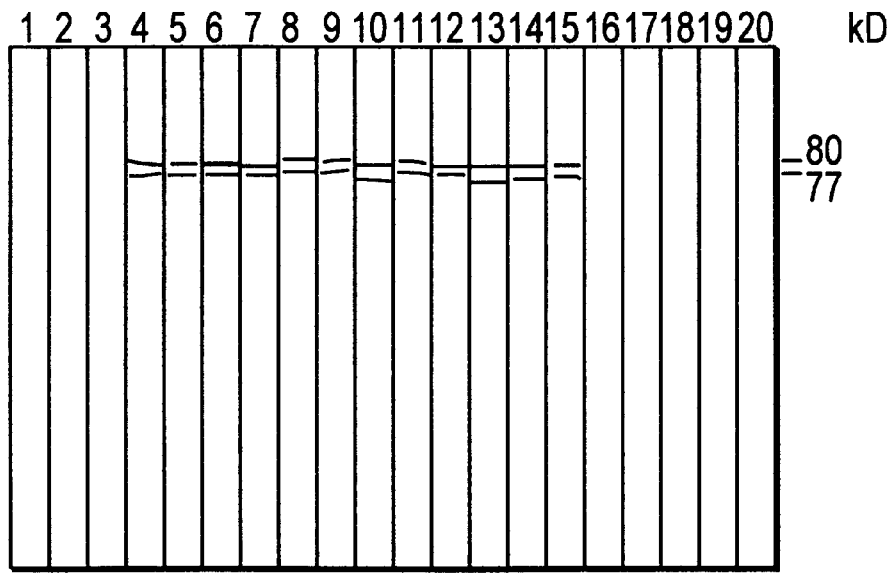
FIG. 3 shows a profile of the Western blot analysis with the serum of a healthy subject or the serum of patients with various autoimmune diseases by using a partially purified fraction of 80 kD.

The band with 80 kD reacted with the sera of 31 out of total 94 patients with rheumatoid arthritis, but did not react with the sera of 20 patients with Systemic Lupus Erythematosus (SLE), or the sera of 20 patients with Progressive Systemic Scleroderma (PSS), and reacted with one serum out of 20 healthy subjects. FIG. 3 shows representative profiles. Lanes 1–3 are the sera of healthy subjects, lanes 4–15 are the sera of patients with rheumatoid arthritis, lanes 16–18 are the sera of patients with PSS, lanes 19–20 are the sera of patients with SLE. It was found that 9 sera out of 31 sera which reacted with the band with 80 kD also reacted with the band with 77 kD.

EXAMPLE 4

Homology of the bands with 80 kD and 77 kD between Mouse and Human

Figure 4:
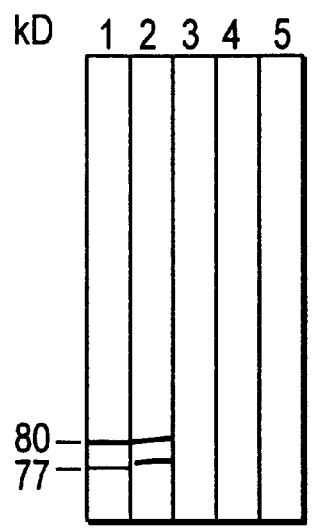
FIG. 4 shows a profile of the Western blot analysis of the serum of a rheumatic patient after the partially purified fraction of MG63 cells derived from human osteosarcoma was subjected to electrophoresis. The serum of a rheumatic patient contained a partially purified fraction of 3T6 cells derived from mouse embryo. The homology of said antigen proteins between human and mouse was examined.

Twelve µl of the partially purified fraction of MG63 derived from human osteosarcoma was subjected to electrophoresis as described in Example 3 and then examined by Western blot analysis. When reacted with the serum of the patient with rheumatoid arthritis (No. 20), a same amount, five times, and 25 times amount of the electrophoresis sample of the partially purified fraction of 3T6 cells derived from mouse embryo was added in order to examine absorption of antibodies. As shown in FIG. 4, by adding 5 times through 25 times amount, the bands with 80 kD and 77 kD disappeared. Lane 1 is a control, lane 2 is the same amount added, lane 3 is 5 times added, lane 4 is 25 times added, and lane 5 is a pattern of Western blot analysis of the serum of a healthy subject. From the result, it was demonstrated that two proteins of 3T6 cells and those of MG63 cells had a similar antigenicity against the serum of the patietn with rheumatoid arthritis and it suggested that these proteins could be the ones which are conserved between mouse and human.

EXAMPLE 5

Amino Acid Sequence Analysis of the Band with 80 kD

Five g of mouse liver powders (Organon Technika Corp.) were suspended in 40 ml of a butter (150 mM NaCl, 1 mM EDTA, 1 mM DTT (dithiothreitol), 0.5 mM PMSF, 0.5 mM benzamidine, 10 mM Tris-HCl, pH 7.5) and centrifuged at 22,000 rpm for 20 minutes. Then, 22.6 g of ammonium sulfate were added per 100 ml of the resulting lysate and centrifuged at 10,000 rpm for 10 minutes. Next, 15.5 g of ammonium sulfate were added per 100 ml of the resulting lysate and centrifuged at 10,000 rpm for 10 minutes. The resulting precipitate was dissolved in 6 ml of a buffer I (10 mM imidazole pH 6.7, 1 mM DTT, 0.5 mM PMSF, 0.5 benzamidine) containing 20 mM NaCl, and then carried out for dialysis against 20 mM NaCl. Then, it was centrifuged at 22,000 rpm for 20 minutes and the resulting lysate was fractionated by hydroxyapatite column chromatography (TSK gel HA-1000, 8.0 mm×750 mm, TOSO Co.) with a linear gradient of 80 mM and 800 mM sodium phosphate pH 7.0. The fractions containing the band with 80 kD were selected and subjected to a reverse-phase HPLC system (Cosmosyl $5C_{18}$-300, 4.6 mm×250 mm Nakaraitesc Co., Ltd.). Approximate 10 µg of the proteins separated by HPLC was enzyme-digested with 10 µl of trypsin in a buffer solution containing 2M urea, 20 mM Tris-HCl, pH 8.0 at 37° C. for 2 hours. The resulting trypsin-peptides were further subjected to the reverse-phase HPLC system (Cosmosyl $5C_{18-300}$) as indicated into 60 fractions. The amino acid sequences of the peptides in 4 fractions out of 60 were analyzed by an autosequencer (model 476A, Applied Biosystems). From the result, 4 peptide-fractions were identified respectively as 73 to 79 amino acid sequences, 152 to 156 amino acid sequences, 166 to 171 amino acid sequences and 172 to 180 amino acid sequences of the amino acid sequences of mouse radixin in FIG. 4 of J. Cell Sci. vol. 103, p.131–143 (1992). The similar experiment was performed by using mouse spleen powders (SIGMA) and the 80 kD protein was identified as 134 to 143 amino acid sequences and 247 to 254 amino acid sequences of mouse ezrin shown in FIG. 4. According to the results, the band with 80 kD was a doublet of 81 kD and 80 kD, and the 81 kD protein and the 80 kD protein were identified as radixin and ezrin, respectively.

EXAMPLE 6

Amino Acid Sequence Analysis of the band with 80 kD

Using 614 mg of 3T6 cells derived from mouse embryo, a partially purified fraction was obtained according to Example 2. The precipitate was dissolved in 2 ml of Dulbecco's PBS and subjected to the reverse-phase HPLC system and fractionated into 88 fractions according to Example 5. Approximate 10 µl of the fraction containing the band with 77 kD was digested according to Example 5 and a trypsin-peptide was obtained. The amino acid sequences of the peptides in 3 peptide fractions were analyzed by the autosequencer (model 476A). From the result, 3 peptide fractions were identified respectively as 41 to 53 amino acid sequences, 156 to 170 amino acid sequences and 171 to 180 amino acid sequences of mouse moesin in the reference described above. From the sequences, the 77 kD protein was identified as moesin.

EXAMPLE 7

Analysis of Reactive Peptides of Radixin and Moesin

One hundred µl each from the 1st to the 60th fractions of HPLC of the trypsin-peptides of radixin according to Example 5 was coated on a mirotiter-plate (4-75078, Nunc) at 45° C., dried overnight, and then blocked with 150 μl of the casein A buffer. Then, 50 μl of the serum of the patient with rheumatoid arthritis (No. 20) which was diluted 400 times with the casein A buffer was added and incubated at room temperate for 60 minutes. Then the resulting was washed out 4 times with Dulbecco's PBS and reacted with biotin-labeled sheep anti-human IgG diluted 5,000 times with the casein B buffer at room temperature for 1 hour.

Then the resulting plate was washed out 4 times with Dulbecco's PBS and further reacted with streptoavidin-peroxidase labeled solution which was diluted 500 times with the casein B buffer for 1 hour. The resulting plate was washed out repeatedly as indicated. Then TMB (tetramethylbenzidine) was added to the plate and the resulting plate was incubated at room temperature for 30 minutes, and 50 μl of 0.5N $H_2SO_4$ was added to stop the reaction. The absorbance of the solution at $OD_{450}$ was measured. The amino acid sequences of the 29th fraction with high antigenicity, e.g. with the highest absorbance peak, was analyzed by the autosequencer (model 476A) and they were shown as SEQ ID NO:1 of the sequence listing.

The 17 to 88 fractions of the trypsin-peptide of moesin fractionated by HPLC system according to Example 6 were treated similarly as indicated, the amino acid sequences of the 60th and the 46th fractions with the highest absorbance peak were analyzed by the autosequencer and they were shown as SEQ ID NO:2 and SEQ ID NO:3 of the sequence listing, respectively.

EXAMPLE 8

Production of Antigen Protein (1) Construction of expression vectors of ezrin, radixin and moesin.

mRNA was isolated from $6 \times 10^7$ cells of MG63 cells derived from human osteosarcoma by using Fast Track mRNA isolation kit (In Vitrogen). cDNA was synthesized from the mRNA using cDNA Synthesis Kit (Pharmacia Biotech). DNA fragments were synthesized by RT-PCR amplification method by using PCR primer EzlS (SEQ ID NO:4), PCR primer Ez2A (SEQ ID NO:5), PCR primer Rd1S (SEQ ID NQ:6), PCR primer Rd2A (SEQ ID NO:7), PCR primer Mo1S (SEQ ID NO:8), and PCR primer Mo2A (SEQ ID NO:9). The amplified fragments were subcloned into pCR™II vector (In Virtogen), respectively. Then they were digested by EcoRV and HindIII and the resulting fragments was ligated into PSEM and expression vectors, pSEM-Ez, pSEM-Rd and pSEM-Mo, were obtained, respectively.

(2) Expression of recombinant protein in *E coli*.

*E. coli* XL1 blue strain was (Stratagene Co.) transformed with the expression vectors, pSEM-Ez, pSEM-Rd and pSEM-Mo, obtained in Example 8 (1) and an expression experiment were performed from a single colony as a seed clone. Four independent clones were spread thoroughly on a LB (luriabetani) plate containing 100 μg/ml ampicillin and stored at 32° C. overnight for cultivation. The bacteria on the plate was collected by a platinum loop, and used to inoculated 3 ml of the LB culture medium containing ampicillin, then incubated with shaking at 32° C. for 1.5 hours. Based on the $OD_{550}$ value of the culture, the culture was used to inoculate 20 ml of the culture medium so as to give $OD_{550}$=0.2, and continued to incubate with shaking. When the value of $OD_{550}$ reached to 0.8 in about 2 hours, isopropyl-1-thio-β-D-galactoside (IPTG) was added to give a final concentration of 1 mM. At 0, 4 and 18 hours from the time of adding IPTG, the culture equivalent to an $OD_{550}$=1.0 was harvested by centrifugation at 15,000 rpm for 2 minutes, suspended in 50 μg/ml of a sample solution (7 M urea, 37.5 mM Tris-HCl, pH 8.8, 1% SDS, 12.5% sucrose, 4% β-mercaptoethanol, 0.5 mg/ml bromophenol blue), boiled for 5 minutes and 7 μl was electophoresed on a 10% polyacrylamide gel. The bacterial culture used for purification of the protein was performed on a 100 ml scale, cultured for 18 to 20 hours after induction and harvested by centrifuging at 6,000 rpm by Hitachi RPR 12-1 rotor for 10 minutes.

(3) Purification

The bacteria was suspended in 10 ml of a TEN buffer (50 mM Tris, pH 7.5, 10 mM EDTA, 10 mM NaCl) and 1 ml of the mixture was distributed into each Eppendorf tube, sonicated for ten times of 2-minute pulse, centrifuged at 15,000 rpm for 10 minutes, and then the precipitate was obtained. The precipitate was washed with a TE buffer (10 mM Tris-HCl, pH 7.5, 1 mM EDTA) containing 100 mM n-octylglucopyranoside. The precipitate was suspended in 200 μl of 7M urea, incubated at 37° C. for 1 hour, centrifuged and the resulting precipitate was eluted with 200 μl of 8M urea, and prepared as an antigen protein.

EXAMPLE 9

Figure 5A:
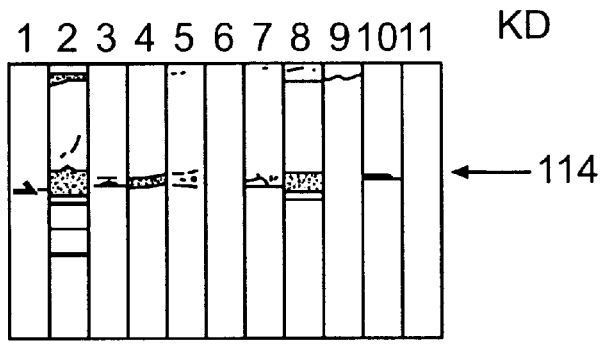
FIG. 5A shows a profile of the Western blot analysis of recombinant ezrin
Figure 5B:
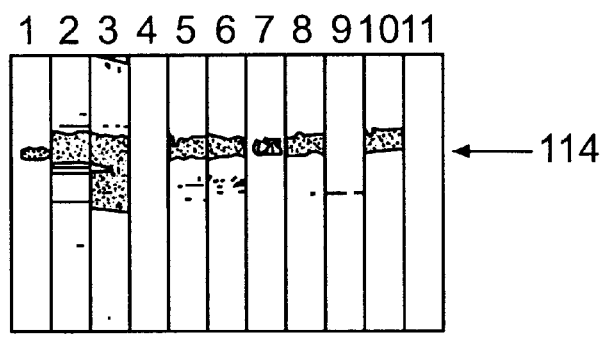
FIG. 5B, shows recombinant radixin
Figure 5C:
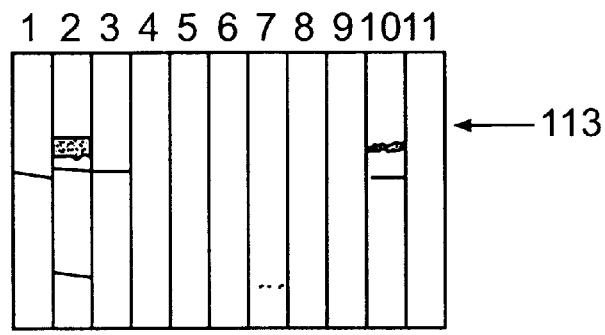
FIG. 5C shows recombinant moesin which were produced from E. coli and were electrophoresed and reacted with the serum of a rheumatic patient. The band is detected as a fusion protein at 114 kD or 113 kD.

Measurement of Anti-Ezrin, Anti-Radixin and Anti-Moesin Antibodies in Sera of Patients Using Recombinant Proteins (1) Western Blot Analysis Two hundred ng per well of the antigen protein obtained in Example 8 was electophoresed and the filter prepared by the similar protocol to Example 3 was reacted at room temperature for 1 hour with the patients' sera diluted 100 times with the casein A buffer containing 100 μg/ml *E. coli* lysate. Then the filter was washed 4 times with Dulbecco's PBS, reacted for 1 hour with horse radish peroxidase (HRPO) conjugated rabbit anti-human IgG, and color was developed by using POD Immuno Stain Set (Wako Pure Chemicals). The electrophoresis pattern of the reactant is shown in FIG. 5. The different reactivities against recombinant ezrin (A), recombinant radixin (B) and recombinant moesin (C) were shown on the patients' sera.

(2) ELISA

The ELISA plates were prepared as follows. Each well of the microtiter plate was coated at 4° C. overnight with 250 ng to 500 ng of the recombinant proteins obtained in Example 8, and then washed three times with a POD solution (Behringwerke AG), and a casein buffer (5% maltose, 0.5% casein, 10 mM Tris-HCl, pH 7.5) containing maltose was added. The resulting plate was stored at room temperature for 2 hours in order to block the reaction, the solution was removed, and the plates were dried overnight in a desiccator.

Figure 6A:
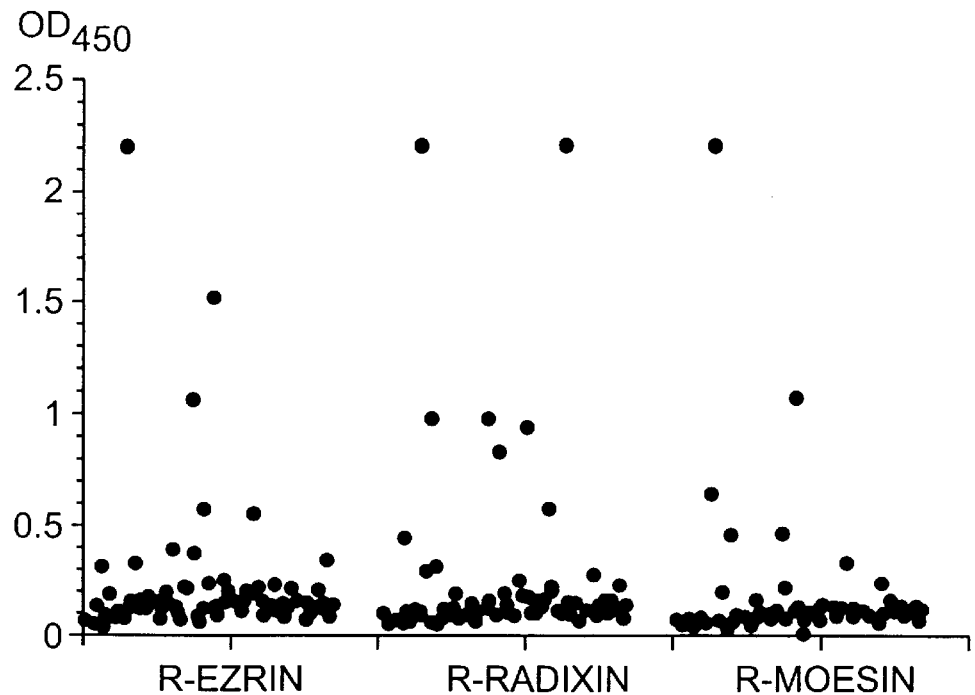
FIGS. 6(A) and 6(B) show the difference of the reactivity between the serum of a rheumatic patient and a healthy subject by ELISA by using recombinant ezrin, recombinant radixin and recombinant moesin are used as an antigen.
Figure 6B:
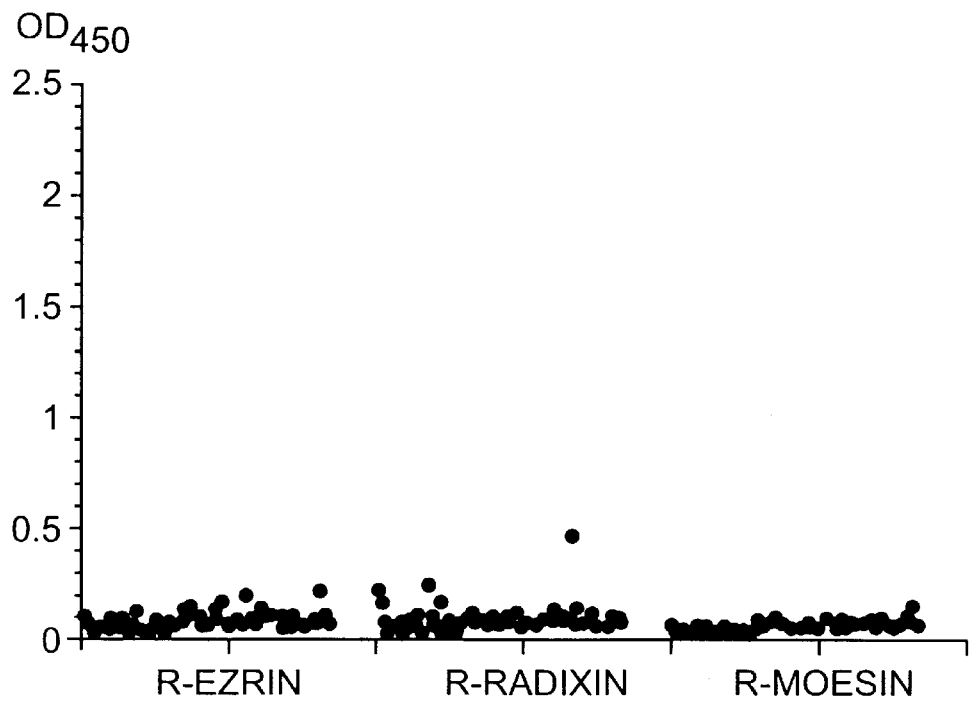

Fifty μl of the patients' sera diluted 400 times with the casein A buffer containing 100 μg/ml *E. coli* lysate was added, and incubated at 25° C. for 60 minutes. After washing 3 times with the POD solution, peroxidase-labeled anti-human IgG was added to the plate, and incubated at 25° C. for 60 minutes, and washed in the same manner. Then, TMB (tetramethylbenzidine) was added in the same manner as in Example 7 so as to develop color. The absorbance at $OD_{450}$ was measured. The results are shown in FIG. 6. While mean ±3SD of the value of the sera of healthy subjects (B) is regarded as a cut-off value ($OD_{450}$=0.19, 0.26, 0.13) against each antigen, a significant high value was measured in the sera of the patients with rheumatoid arthritis. Therefore, the present ELISA system enables precritical or early diagnosis of rheumatism.

UTILIZED POSSIBILITY IN INDUSTRY

As clearly observed in the results as described, a method can be established for precritical or early diagnosis of rheumatism, by way of immunologically detecting antibodies in the serum of a rheumatic patient which are reacted with autoantigen proteins (ezrin, radixin and moesin) of mammalian origin. Further, the method of immunologically detecting autoantigen is convenient, reliable and highly advantageous for diagnosis of the serum at early stage, based on the rheumatic specific antigens.

We claim:

1. A method of detecting autoantibodies in the sera of patients with rheumatism, by reacting one or more proteins selected from the group consisting of ezrin, radixin, and moesin of mammalian origin and/or one or more peptides comprising at least 9 or more consecutive amino acid residues found in the amino acid sequence in the group selected from ezrin, radixin, and moesin with human sera, wherein said peptides bind to said autoantibodies.

2. The method of detecting autoantibodies in the sera of patients with rheumatism as claimed in claim 1, wherein radixin is reacted with human sera.

3. The method of detecting autoantibodies in the sera of patients with rheumatism as claimed in claim 1, wherein radixin and moesin are reacted with human sera.

4. The method of detecting autoantibodies in sera of patients with rheumatism as claimed in claim 1, wherein ezrin, radixin and moesin are reacted with human sera.

* * * * *

SEQUENCE LISTING

```
<160> NUMBER OF SEQ ID NOS: 9

<210> SEQ ID NO 1
<211> LENGTH: 9
<212> TYPE: PRT
<213> ORGANISM: Mus musculus

<400> SEQUENCE: 1

Ile Gln Asn Trp His Glu Glu His Arg
 1               5

<210> SEQ ID NO 2
<211> LENGTH: 13
<212> TYPE: PRT
<213> ORGANISM: Mus musculus

<400> SEQUENCE: 2

Gly Met Leu Arg Glu Asp Ala Val Leu Glu Tyr Leu Lys
 1               5                  10

<210> SEQ ID NO 3
<211> LENGTH: 31
<212> TYPE: PRT
<213> ORGANISM: Mus musculus

<400> SEQUENCE: 3

Thr Ala Met Ser Thr Pro His Val Ala Glu Pro Ala Glu Asn Glu His
 1               5                  10                  15

Asp Glu Gln Asp Glu Asn Gly Ala Glu Ala Ser Ala Glu Leu Arg
            20                  25                  30

<210> SEQ ID NO 4
<211> LENGTH: 24
<212> TYPE: DNA
<213> ORGANISM: Unknown
<220> FEATURE:
<223> OTHER INFORMATION: Description of Unknown Organism: PCR primer DNA
      named Ez1S

<400> SEQUENCE: 4
aatcaatgtc cgagttacca ccat                                          24

<210> SEQ ID NO 5
<211> LENGTH: 24
<212> TYPE: DNA
<213> ORGANISM: Unknown
<220> FEATURE:
<223> OTHER INFORMATION: Description of Unknown Organism: PCR primer DNA
      named Ez2A

<400> SEQUENCE: 5
cgtttccttt aatgatgctg actc                                          24

<210> SEQ ID NO 6
```

```
<211> LENGTH: 23
<212> TYPE: DNA
<213> ORGANISM: Unknown
<220> FEATURE:
<223> OTHER INFORMATION: Description of Unknown Organism: PCR primer DNA
      named Rd1S

<400> SEQUENCE: 6
gaaaatgccg aaaccaatca acg                                             23

<210> SEQ ID NO 7
<211> LENGTH: 24
<212> TYPE: DNA
<213> ORGANISM: Unknown
<220> FEATURE:
<223> OTHER INFORMATION: Description of Unknown Organism: PCR primer DNA
      named Rd2A

<400> SEQUENCE: 7
ctgcttttct ctgttggtgg ttca                                            24

<210> SEQ ID NO 8
<211> LENGTH: 24
<212> TYPE: DNA
<213> ORGANISM: Unknown
<220> FEATURE:
<223> OTHER INFORMATION: Description of Unknown Organism: PCR primer DNA
      named Mo1S

<400> SEQUENCE: 8
tgcctttgcc gccaccatgc ccaa                                            24

<210> SEQ ID NO 9
<211> LENGTH: 24
<212> TYPE: DNA
<213> ORGANISM: Unknown
<220> FEATURE:
<223> OTHER INFORMATION: Description of Unknown Organism: PCR primer DNA
      Ez1S

<400> SEQUENCE: 9
cctagaccgc atacactcca ccgt                                            24
```